United States Patent [19]

Abraham et al.

[11] Patent Number: 5,668,182
[45] Date of Patent: Sep. 16, 1997

[54] METHOD OF CALMING OR SEDATING AN ANIMAL WITH A HYDROXY BENZALDEHYDE COMPOUND

[75] Inventors: Donald J. Abraham, Midlothian; Louis S. Harris; B. J. Meade, both of Richmond; Albert E. Munson, Midlothian; Paul S. Swerdlow; Graham A. Patrick, both of Richmond, all of Va.

[73] Assignee: Virginia Commonwealth University, Richmond, Va.

[21] Appl. No.: 699,640

[22] Filed: Aug. 19, 1996

[51] Int. Cl.⁶ .................. A61K 31/11; A61K 31/235; A61K 31/19

[52] U.S. Cl. .................. 514/699; 514/544; 514/545; 514/532; 514/705; 514/568; 514/570

[58] Field of Search .................. 514/699, 544, 514/545, 532, 705, 568, 570

[56] References Cited

U.S. PATENT DOCUMENTS

| | | |
|---|---|---|
| 4,267,185 | 5/1981 | Finizio . |
| 4,351,836 | 9/1982 | Rajagopalan . |
| 4,582,705 | 4/1986 | Primes et al. . |
| 4,751,244 | 6/1988 | Abraham et al. . |
| 5,043,350 | 8/1991 | Pennev et al. . |
| 5,254,569 | 10/1993 | Cheeseman et al. . |

OTHER PUBLICATIONS

D. Abraham, et al., Vanillin, A Potential Agent for the Treatment of Sickle Cell Anemia; Blood, vol. 77, No. 6, Mar. 15, 1991; pp. 1334–1341.

*Primary Examiner*—William R. A. Jarvis
*Attorney, Agent, or Firm*—Whitham, Curtis, Whitham & McGinn

[57] ABSTRACT

Various hydroxy benzaldehyde derivatives including Vanillin, a natural product derived from the vanilla bean that is commonly used as a flavoring agent, is administered by injection (i.v., i.m., s.c., and the like) or intravenous infusion in an effective dose amount to a patient in need of calming or sedation.

7 Claims, No Drawings

METHOD OF CALMING OR SEDATING AN ANIMAL WITH A HYDROXY BENZALDEHYDE COMPOUND

BACKGROUND OF THE INVENTION

1. Field of the Invention

The invention is generally related to a psychotherapeutic use for the natural product vanillin and derivatives of vanillin.

2. Description of the Prior Art

Vanillin has the chemical name 4-hydroxy-3-methoxybenzaldehyde and the chemical structure:

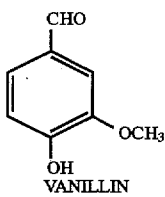

VANILLIN

Vanillin occurs naturally in vanilla beans, potato parings, and Siam benzoin, and is produced synthetically from eugenol or guaiacol or from the lignin waste from the wood pulp industry.

Vanillin is relatively nontoxic; the Merck index reports an oral $LD_{50}$ for vanillin of 1580 mg/kg in rats. The relative safety of vanillin is further borne out by the fact that it was given GRAS (i.e., "generally regarded as safe") status by the Flavor and Extract Manufacturer's Association (FEMA) and was recognized for food use by the Food and Drug Administration (FDA). In man, vanillin is converted to vanillic acid in the liver and is excreted in the urine.

The vanillin compound is devoid of nitrogen, unlike many of the conventionally-prescribed tranquilizer and/or sedative compounds, such as the family of drugs known as benzodiazepines. The benzodiazepines include diazepam (e.g., such as marketed under the brand name "Valium") and chlordiazepoxide (e.g., such as marketed under the brand name "Librium"), and they are central nervous system (CNS) depressants. These benzodiazepines are generally effective for relief of symptoms of anxiety, tension, fatigue or agitation and present a low risk of lethality in humans when taken alone (e.g., diazepam has an oral $LD_{50}$ of 1240 mg/kg in rats). They nonetheless can have serious adverse side effects. For instance, known reported side effects of these benzodiazepines include the fact that they can be abused if taken for extended periods of time; also withdrawal symptoms can occur upon discontinuance of the therapy; they are subject to certain drug interaction concerns; and they may cause birth defects in first trimester fetuses, and/or make the fetus dependent upon the drug, and they can even be transmitted from a medicated mother to newborn infants through breast milk. Therefore, there are certain serious risks associated with administering benzodiazepines to women of child-bearing age, in particular, unless an appropriate prior investigation is made before they are administered to this class of patients.

By contrast, vanillin is commonly used in relatively trivial concentrations as a flavoring agent in confectionery, beverages, foods, tobacco; and as a scent in perfumery. The highest average national level of use reported is 768 ppm, in confectionaries and frostings, and possible average daily intake of vanillin from foods has been estimated as 38.9 mg/capita, as reported by the National Technical Information Service, US Dept. of Commerce, Springfield, Va. 22161, Report fda/bf-78/157 Scientific Literature Review of Vanillin and Derivatives in Flavor Usage, August 1978, p 4.

Vanillin also has been used in trivial amounts for the limited purpose of flavoring dosage forms of pharmaceutically active agents to encourage patient acceptance. For example, U.S. Pat. No. 4,267,185 (Finizio) describes benzenobenzisoquinoline derivatives useful as antidepressants that can be administered, among other ways, in the form of a suspension flavored with a relatively small amount of vanillin. Similarly, U.S. Pat. No. 4,351,836 (Rajagopalan) describes pyrrolylpiperidines useful as antidepressants that can administered, among other ways, in the form of a suspension flavored with a very small amount of vanillin. Also, the use of vanillin as a flavorant for dosages of (amidomethyl)nitrogen heterocyclic and pyrrolidine compounds used for analgesics, diuretics, and so forth, is described in U.S. Pat. No. 5,254,569 (Cheeseman et al.). Similarly, U.S. Pat. No. 5,043,350 (Pennev et al.) discloses vanillin as a flavorant for doses of benzo-fused cycloalkane and oza- and thia-cycloalkane trans- 1,2-diamine compounds useful as analgesics and/or diuretics. The optional use of vanillin as a flavorant for an electrolyte stabilizing composition used for detoxifying chronic alcoholics and hard-line drug addicts while avoiding major withdrawal symptoms is mentioned in U.S. Pat. No. 4,582,705 (Primes et al.).

An actual medicinal use of vanillin for the limited purpose of treating of sickle cell anemia, a blood disorder, has been reported by D. Abraham, et al., "Vanillin, a Potential Agent for the Treatment of Sickle Cell Anemia," Blood, Vol. 77, No. 6 (March 15) 1991: pp. 1334–1341.

However, there is an unsatisfied need in the prior art of psychotherapy for a central nervous system (CNS) depressant agent that poses less risk of adverse side effects and other pernicious effects to the host.

SUMMARY OF THE INVENTION

It is an object of this invention to provide a new use for vanillin.

According to the invention, it has been found that vanillin can be used as a short term, psychotherapeutic agent in mammalian recipients.

In one aspect, the vanillin is administered by injection at a dose of at least about 200 mg/kg body weight of a rodent host, preferably a dose in the range of about 200 to about 1,500 mg/kg. The optimal dose for humans ranges from about 2.0 to about 3.0 mg/kg body weight. When so administered, vanillin has been discovered to exhibit properties characteristic of CNS depressants in mammalian subjects. These uncovered attributes of vanillin show it to be suitable for use in treatment of anxiety and anxiety disorders, such attributes including short term muscle relaxation and impairment, suppression of small motor movements without affecting gross motor movements in the host, enhancement of the duration of barbituate-induced loss of righting reflex, and anticonvulsant activity. The vanillin molecule is devoid of nitrogen, and it represents a relatively safe, non-toxic tranquilizing agent.

For purposes of this invention, "vanillin" means 4-hydroxy-3-methoxybenzaldehyde having the following chemical structure:

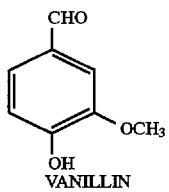

VANILLIN

DETAILED DESCRIPTION OF THE PREFERRED EMBODIMENTS OF THE INVENTION

The invention relates to the psychotherapeutic use for the natural product vanillin and derivatives of vanillin. This psychotherapeutic use of vanillin encompasses its use as an anti-anxiety agent, an anticonvulsant, and/or as a sedative (sleeping drug).

It has been found that vanillin mimics the effects of conventional tranquilizers such as those of the benzodiazepine family, in that it relaxes the large skeletal muscles and has a direct effect on the brain. In doing so, vanillin has been found to relax the host and make the host more tranquil, or sleepier (e.g., if used as an adjunct with a sleep-inducing barbituate such as pentobarbital). The vanillin is especially effective for short term duration after administration in these psychotherapeutic uses while being extremely safe and without causing the adverse side effects often associated with many conventional tranquilizers.

Also, the inventive effect, while optimal for vanillin, is not limited thereto, and includes derivatives and analogs of vanillin, where these compounds can be represented by the following general formula:

wherein X can be —CHO or —$(CH_2)_n$—$COOR_1$ where n is an integer having a value of 0 to 9 and $R_1$ is a lower alkyl group (e.g., 1–5 carbon atoms) such as methyl, Y can be —OH or —$OR_2$ where $R_2$ can be a benzyloxyl group or a carboxylbenzyloxyl group, and Z can be —$OR_3$ where $R_3$ can be a lower alkyl group (e.g., 1–5 carbon atoms) such as methyl, —COOH, or —O—$(CH_2)_q$—COOH where q is an integer value of 1 to 9.

Representative specific examples of compounds contemplated for use in this invention as the psychotherapeutic agent include the following:

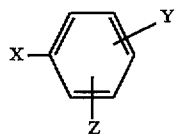

VANILLIN

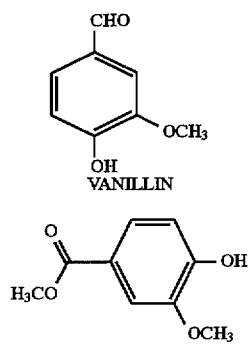

TBJ1: Methyvanillate

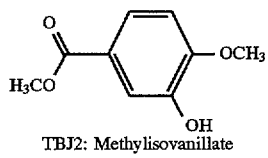

TBJ2: Methylisovanillate

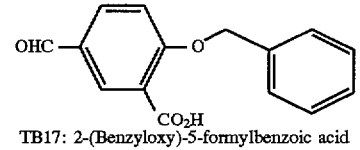

TBJ3: Methylhomovanillate

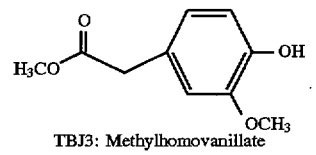

TB17: 2-(Benzyloxy)-5-formylbenzoic acid

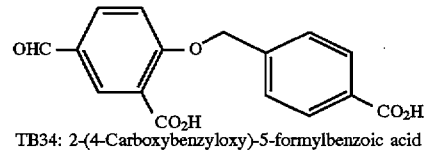

TB34: 2-(4-Carboxybenzyloxy)-5-formylbenzoic acid

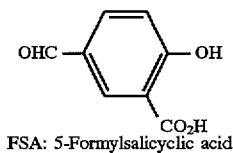

FSA: 5-Formylsalicyclic acid

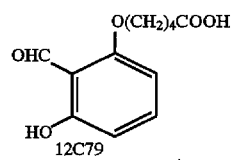

12C79
2-carboxybutoxy-6-hydroxy-benzaldehyde

Preferred compounds include vanillin and its methylvanillate derivatives, such as compounds represented by compounds TBJ1, TBJ2, and TBJ3.

The optimum delivery routes for the vanillin include i.v. injection (i.e., intravenous injection), i.m. injection (i.e., intramuscular injection), and s.c. injection (i.e., subcutaneous injection), and the like, in sterile liquid dosage forms. For non-human recipients, the delivery route for the vanillin also includes i.p. injection (i.e., intraperitoneal injection). Optimal CNS depressant effects are observed for the present invention where relatively high doses of vanillin are administered directly into the bloodstream of the host. The host for the psychotherapeutic treatment with vanillin generally are mammalian, such as rodents and humans. The optimal dose for rodents is at least about 200 mg/kg body weight, preferably a dose in the range of about 200 to about 1,500 mg/kg. The optimal dose for humans ranges from about 2.0 to about 3.0 mg/kg body weight. As sources of vanillin, vanillin concentrate can be purchased from Aldrich Chemical Company (Milwaukee, Wis.) and Sigma Chemical Company (St. Louis, Mo.).

In the following examples, objects and advantages of this invention are further illustrated by various embodiments thereof but the details of those examples should not be construed to unduly limit this invention. All parts and percentages therein are by weight unless otherwise indicated.

EXAMPLES

Studies were performed to investigate and confirm the depressant effects of vanillin with regard to relative potency, duration of action, qualitative similarity to conventional sedative drugs, as well as to examine the generality of sedative effect across species of rodents.

Example 1

To assess behavioral depression in rats as induced by vanillin, male and female rats, five of each gender at each dose, were given doses of vanillin of 50, 100 or 200 mg/kg, respectively, or a control vehicle (0.9% sodium chloride in water) by intravenous (i.v.) infusion. Therefore, there were four groups of rats with ten rats per group tested at each dosage. The solution was infused into a tail vein through a butterfly cannula, with the infusion being performed at a constant rate over a 5-minute period using a Harvard infusion pump. As soon as possible (<120 seconds) after the termination of infusion, a rat was observed for loss or suppression of corneal reflex, withdrawal on pinch, loss of righting reflex ("sleep time"), ability to stand, ability to walk, and assigned a numerical score (0 to 8) for the collection of responses observed based on the rating scale summarized below in Schedule A. The test subject rats were also tested for grip (the complete absence or visually detectable substantial impairment in resistance to being pulled by the tail across a wire cage bottom by comparison to behavior of the control animals) and were observed for spontaneous ambulation and/or exploratory movement.

Schedule A

| Score | Corneal Reflex | Withdrawal on Pinch | Righting Reflex Loss | Can Stand | Can Walk |
| --- | --- | --- | --- | --- | --- |
| 0 | + | + | + | + | + |
| 1 | + | + | + | + | +/0 |
| 2 | + | + | + | + | 0 |
| 3 | + | + | + | +/0 | 0 |
| 4 | + | + | + | 0 | 0 |
| 5 | + | + | +/0 | 0 | 0 |
| 6 | + | + | 0 | 0 | 0 |
| 7 | + | 0 | 0 | 0 | 0 |
| 8 | 0 | 0 | 0 | 0 | 0 |

+: Normal response; sign is present
+/0: Delayed response, or mixed response
0: No response; sign is not present The evaluation of each rat was repeated at 10, 20, 30, 45, 60, 90 and 120 minutes after termination of the infusion, or until the rat exhibited normal behavior. The evaluations were performed on days 1, 3, 5 and 9 of vanillin administration.

Intravenous infusion of vanillin on day 1 of the study did produce relatively short-lived signs of depression in the rats, as indicated in Table 1 below (the results are abridged to show those observed for the first 45 minutes). The signs were distinctly observed with appreciable frequency at the highest dose administered of 200 mg/kg. Some of the rats were rendered temporarily unable to walk, although the ability to walk returned within less than 10 minutes. However, a larger number of animals did not initiate ambulation, but could and did move about if prodded. The most prevalent and most persistent effect of vanillin was on grip strength, which was weakened in most rats by the intermediate dose of vanillin and was obliterated by the highest dose. This effect was noticeably diminished within 10 minutes, but some slight effect persisted for 45 minutes or more following the highest dose. The result suggests a muscle relaxing effect induced by the vanillin. In no case was there any observable difference between male and female rats, so all rats at a given dose have been grouped together for the presentation of data without distinction made as to gender. Although it was not a sign that was included in the examination protocol, it was noted that several rats in the intermediate and high dose groups would close their eyes either partially or completely following the vanillin, but they would open them in response to external stimulation. This effect typically appeared within 10 minutes after infusion and persisted for up to 45 minutes.

TABLE 1

| Sign of Depression | Vanillin Dose (mg/kg) | Time after Treatment (min) | | | | |
| --- | --- | --- | --- | --- | --- | --- |
| | | <2 | 10 | 20 | 30 | 45 |
| Score > 0 | 0 (control) | 0 | 0 | 0 | 0 | 0 |
| | 50 | 0 | 0 | 0 | 0 | 0 |
| | 100 | 0 | 0 | 0 | 0 | 0 |
| | 200 | 3 | 0 | 0 | 0 | 0 |
| Grip Absent/ Grip Weak | 0 (control) | 0/0 | 0/0 | 0/0 | 0/0 | 0/0 |
| | 50 | 0/1 | 0/0 | 0/0 | 0/0 | 0/0 |
| | 100 | 0/6 | 0/2 | 0/0 | 0/0 | 0/0 |
| | 200 | 10/10 | 0/8 | 0/8 | 0/5 | 0/2 |
| Ambulation Absent | 0 (control) | 0 | 0 | 0 | 0 | 0 |
| | 50 | 0 | 0 | 0 | 0 | 0 |
| | 100 | 0 | 0 | 0 | 0 | 0 |
| | 200 | 5 | 0 | 0 | 0 | 0 |

The observations on days 3, 5 and 9 of infusion were qualitatively similar and were generally unremarkable, so they are not specifically reported here in detail.

Therefore, vanillin was observed to possess properties characteristic of CNS depression in rats. When given alone, its effects on righting reflex and on motor coordination appear mild and transient. However, in the rats it did produce mild muscle relaxation that persisted for 30 to 45 minutes.

It was noted on days 5 and 9 that there was some suggestion of tolerance being developed by the rats to several of the depressant effects. For example, on those days no rats were rated with depression scores above zero. Secondly, only 4 of 10 rats at the highest dose displayed absence of grip, and 1 rat exhibited no muscular or motor impairment at all. Almost all of those rats that did exhibit diminished grip returned to normal within 20 minutes, i.e., more quickly than was observed on day 1. Finally, another general observation was that the number of rats exhibiting eye closure was smaller on the later days, and the duration of the closure was shorter.

Example 2

The depressant effect of vanillin on mice was investigated by examining the effect of vanillin on pentobarbital-induced loss of righting reflex. Groups of mice (six to fourteen mice per group) were designated to receive a dose of vanillin of 50, 100, 200 or 300 mg/kg, or a control vehicle (0.9% sodium chloride in water). Fifty (50) mg/kg I.p. (intraperitoneally) injected pentobarbital was administered to each mouse of each group, and each mouse was also concurrently given the dose of vanillin (50, 100, 200 or 300 mg/kg) or the control vehicle, depending on its grouping, by s.c. (subcutaneous) injection.

The effects of vanillin on the onset and duration of "sleep" induced by the pentobarbital were observed. That is, the time required for each mouse to lose its righting reflex (onset of action) was noted for the higher doses, and the time required for each mouse to regain the righting reflex (duration of "sleep") was determined. Means and standard errors of values for onset and duration of "sleep" were determined for each experimental group. Each vanillin-treated group was compared with its concomitantly tested control group (treated with saline in lieu of vanillin) for evaluating the statistical significance of vanillin effect. The results are summarized in Table 2.

TABLE 2

| Dose of vanillin | Onset of "sleep"(min) (mean + SEM) | | Duration of "Sleep"(min) (mean + SEM) | |
|---|---|---|---|---|
| (mg/kg) | Vehicle | Vanillin | Vehicle | Vanillin |
| 50 | — | — | 31.0 ± 3.79 | 20.3 ± 1.09* |
| 100 | — | — | 36.5 ± 4.67 | 47.6 ± 4.48 |
| 200 | 3.5 ± 0.87 | 2.8 ± 0.97 | 27.4 ± 3.34 | 62.9 ± 5.05** |
| 300 | 4.3 ± 0.97 | 3.3 ± 0.23 | 39.6 ± 6.57 | 102.1 ± 5.71** |

*significantly different from control at p<0.05
**significantly different from control at p<0.001

The results demonstrate that when vanillin was given in the relatively higher doses of 100 to 300 mg/kg along with pentobarbital that the duration of loss of righting reflex in mice was markedly increased and enhanced.

Three types of activity measures were automatically recorded by the system: (1) all interruptions of all beams were recorded as "Total activity counts"; (2) interruptions of two consecutive beams were recorded as "Ambulatory activity counts"; and (3) interruptions of four consecutive beams were recorded as "Gross movements".

The effects of doses of vanillin (200 and 300 mg/kg i.p.) was assessed and compared with locomotor activity recorded for concomitantly tested mice given only vehicle (0.9% NaCl in water). Measurement of locomotor activity was made during 10 minute intervals for 60 minutes after treatment. Due to the relatively short duration of vanillin encountered, the higher dose group also had measurements taken at three minute intervals for 24 minutes and at one minute intervals for nine minutes after treatment.

Means and standard errors of numbers of counts were determined for each experimental group. The results are summarized in Table 3.

TABLE 3

| Dose (mg/kg) | Time Interval after Treatment (min) | | | | | |
|---|---|---|---|---|---|---|
| Vanillin: | 0–10 | 10–20 | 20–30 | 30–40 | 40–50 | 50–60 |
| Activity Measure | | | | | | |
| 0 (control) | | | | | | |
| Total | 1525 ± 281 | 832 ± 105 | 582 ± 126 | 635 ± 204 | 268 ± 167 | 663 ± 47 |
| Ambulatory | 739 ± 108 | 461 ± 68 | 307 ± 76 | 599 ± 224 | 171 ± 103 | 430 ± 33 |
| Gross | 83 ± 16 | 41 ± 8 | 34 ± 13 | 31 ± 11 | 19 ± 14 | 23 ± 8 |
| 200 | | | | | | |
| Total | 897 ± 201 | 399* ± 46 | 481 ± 257 | 410 ± 275 | 413 ± 115 | 245* ± 50 |
| Ambulatory | 545 ± 62 | 291 ± 37 | 130 ± 85 | 409 ± 276 | 243 ± 67 | 192* ± 37 |
| Gross | 86 ± 16 | 43 ± 8 | 18 ± 13 | 14 ± 11 | 32 ± 13 | 31 ± 8 |
| 300 | | | | | | |
| Total | 648* ± 190 | 449 ± 155 | 404 ± 176 | 441 ± 121 | 365 ± 108 | 156* ± 86 |
| Ambulatory | 479 ± 150 | 298 ± 117 | 245 ± 100 | 270 ± 74 | 244 ± 66 | 83* ± 48 |
| Gross | 75 ± 23 | 57 ± 19 | 37 ± 16 | 38 ± 10 | 21 ± 8 | 12 ± 7 |

*significantly different from control at p≧0.05

The magnitude of this effect was surprising, especially in light of the observation that the lower dose of vanillin (viz. 50 mg/kg) appeared to impart the opposite effect; that is, the lower dosage of vanillin appeared to lessen the barbituate effect. Therefore, higher doses of vanillin were found to enhance barbituate-induced loss of righting reflex.

Example 3

The effect of vanillin on spontaneous locomotor activity of mice was examined. Three groups of male mice, with four mice per group, were assigned to receive a dosage of vanillin of 0, 200 or 300 mg/kg, respectively. After i.p. injection of vanillin or a control solution (0.9% NaCl in water), an injected mouse was placed by itself in a cage, the cage enclosed in a cabinet to exclude external stimuli, and locomotor activity of the mouse was monitored. Three types of movements of the mouse within the cage were measured, based upon interruptions of 16 beams of infrared light, spaced one inch (2.54 cm) apart, which traverse the cage. Interruptions of the infrared beams are detected by sensors and are recorded as "counts" of activity using a system obtained from Omnitech Electronics, Columbus Ohio.

The effects of vanillin on locomotor activity were relatively mild although unusual in character. Gross movements, such as walking, were not significantly affected at any time by doses of vanillin up to 300 mg/kg. In contrast, the smaller types of motor movements were observed to be suppressed by vanillin. These activities included stereotypic movements, such as grooming, and other activities performed essentially "in place". This selective depression of only smaller movements is not typical of general CNS drugs. The effect is rather irregular, both in dose-relatedness and in its time course. Some effect does seem to persist for 60 minutes or more following vanillin administration.

Example 4

An inverted screen test was performed on mice to investigate the effect of vanillin and vanillin analogs on muscular function. After i.p. injection of vanillin or vehicle, each mouse was placed on a wire screen (12.8 cm×12.8 cm with a 6 mm mesh size) and the screen was inverted. A positive effect was found if the drug caused the mouse to fall from the screen within 60 seconds. A negative effect was found if the mouse had the ability to climb from the underside of the screen to the top side of the screen within the 60 second time period. Hanging from the underside of the screen without falling but without climbing to the topside at 60 seconds is recorded as a one-half positive effect per the convention of Coughenour, L. L.; Mclean, J. R.; Parker, R. B., "A New Device for the Rapid Measurement of Impaired Motor Function in Mice," Pharmacol. Biochem. Behav., 6: 351–353; 1977. The test was performed at 2, 5, 10, and 30 minutes following administration of vanillin or vehicle. At each of those times, an ED-50 (and 95% confidence limits) was determined for vanillin. Six mice were used in each experimental group.

Several analogs of vanillin were also examined in this test. The chemical structures and chemical names for these compounds are described hereinabove.

The testing of these compounds was limited both by supply of compound and by solubility. Testing was performed at 2, 5, 10, 20 minutes after administration of drug or vehicle. The vehicles used to solubilize the analogs were as follows: 10% ethanol for TBJ1, TBJ2, and TBJ3; 3% ammonium hydroxide solution in saline for FSA (pH=9); 6.7% ammonium hydroxide in saline for TB17 (pH=9.3); and 20% ethanol, 1% ammonium hydroxide solution in saline for TB34 (pH=10.0). ED-50s of compounds (and 95% confidence limits) were calculated in cases where the data permitted the calculation.

As shown in Table 4 below, vanillin produced a dose-related deficit in performance in the inverted screen task, demonstrating impairment of muscular function. The ED-50 for vanillin was consistently around 100 mg/kg for the first 10 minutes after injection, bit its potency declined precipitously between 10 and 30 minutes after injection. Analogs of vanillin were rather variable in their effects on performance in this procedure. As can be seen in Table 4, TBJ2 and TBJ3 were approximately equipotent to vanillin at the early time points (up to 5 minutes), but the assessment of relative effects is confounded by the fact that the ethanol-containing vehicle used to solubilize these compounds produces approximately 10% impairment itself of performance at those times. The effect of TBJ2, particularly at the highest dose (200 mg/kg) persisted for 20 minutes after treatment, while that of TBJ3 had essentially abated by 10 minutes after injection.

Other tested analog compounds, not included in Table 4, generally either failed to affect performance (viz., FSA and TB17) or produced mild or erratic effects (viz. TB34). An exception was TBJ1, which produced significant effects (100% at 5 minutes and 75% at 20 minutes) at 200 mg/kg, but TBJ1 did not produce significant effects at lower doses, so a meaningful ED-50 could not be calculated for that analog trial.

TABLE 4

| Time post-treatment | ED-50 (mg/kg) (95% confidence limits) | | |
|---|---|---|---|
| (min) | Vanillin | TBJ2 | TBJ3 |
| 2 | 112 (75–168) | ~100 | — |
| 5 | 104 (70–156) | >100 | 99.7 (62.5–159) |
| 10 | 112 (75–168) | 132 (95–184) | inactive at 200 |
| 30 | 748 (85–6560) | ~140 (at 20 min) | — |

The vanillin exhibited a consistent dose-related depressant effect in terms of its ability to impair motor performance in the inverted screen test. This effect was pronounced, although abated significantly by 30 minutes after administration. Several of the tested analogs, viz., TBJ2 and TBJ3, share this effect, but none appeared to be significantly more potent than vanillin itself, and only one, TBJ2, appeared to be approximately equipotent and as long or longer acting. All of the tested analogs with activity in this test exhibited a more erratic dose-response relationship than vanillin. The observed effects of vanillin and its congeners in this test, along with the observed effects of vanillin on small movements in locomotor activity reported in Example 3, indicate a utility for vanillin in producing muscle relaxation when a sufficient duration is obtained.

Example 5

Mice were treated with vanillin (100, 200, or 300 mg/kg) or saline (0.9% NaCl) by i.p. injection. The treatment was followed either by injection of pentylenetetrazol ("Metrazol"), 80 or 90 mg/kg by i.p. injection (given 5 minutes after vanillin) or by exposure to a 1-second pulse of shock through electrodes clamped to the ears (5 minutes after vanillin). The end-points for both tests were the occurrence of a tonic (extensor) convulsion and/or death. Six mice were used per group for the Metrazol-induced seizure test, and five mice were used per group for the electroshock-induced seizure test. The results are reported in Table 5 below.

TABLE 5

| Metrazol-induced Seizures: | | |
|---|---|---|
| Treatment | Tonic Convulsion | Death |
| Metrazol 90 mg/kg + vehicle | 6/6 | 0/6 |
| vanillin 200 mg/kg | 5/6 | 2/6 |
| vanillin 300 mg/kg | 1/6 | 0/6 |
| Electroshock-induced Seizures: | | |
| Electroshock after vehicle | 5/5 | 1/5 |
| vanillin 300 mg/kg | 4/5 | 0/5 |

The data summarized in Table 5 suggest that vanillin possesses some mild anticonvulsant activity, particularly at higher doses. The 300 mg/kg dose of vanillin did appear to afford some protection versus Metrazol-induced seizures.

While the invention has been described in terms of its preferred embodiments, those skilled in the art will recognize that the invention can be practiced with modification within the spirit and scope of the appended claims.

We claim:

1. A method of calming or sedating a host animal in need thereof, comprising the step of:

administering to said host animal by injection or intravenous infusion an effective dose of a compound of the formula:

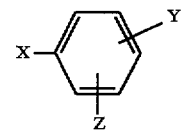

wherein X is —CHO or —(CH$_2$)$_n$—COOR$_1$ where n is an integer value of 0 to 9 and R$_1$ is a 1C to 5C alkyl group, Y is —OH or —OR$_2$ where R$_2$ is a benzyloxyl or a carboxylbenzyloxyl group, and Z is —OR$_3$ where R$_3$ is a 1C to 5C alkyl group, —COOH, or —O—(CH$_2$)$_q$—COOH where q is an integer value of 1 to 9.

2. The method of claim 1 wherein said host is a mammal.

3. The method of claim 1 wherein said host is human and said effective dose of said compound ranges from about 2.0 to about 3.0 mg/kg body weight of said host.

4. The method of claim 1 wherein said step of administration is performed by a delivery route selected from the group consisting of i.m. injection, s.c. injection, and i.v. injection.

5. The method of claim 1 wherein said compound is vanillin.

6. The method of claim 1 wherein said compound is a hydroxy benzaldehyde compound selected from the group consisting of

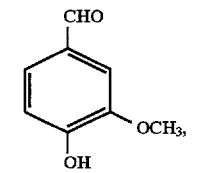

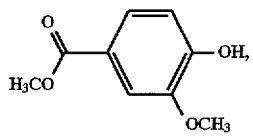

-continued

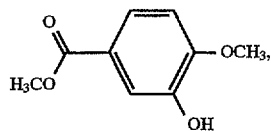

and

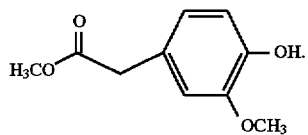

7. The method of claim 1 wherein said compound is a hydroxy benzaldehyde compound.

* * * * *